(12) United States Patent
Norimoto

(10) Patent No.: US 8,864,731 B2
(45) Date of Patent: Oct. 21, 2014

(54) ABSORBENT ARTICLE

(75) Inventor: Yoshimi Norimoto, Sakura (JP)

(73) Assignee: Daio Paper Corporation, Ehime (JP)

( * ) Notice: Subject to any disclaimer, the term of this patent is extended or adjusted under 35 U.S.C. 154(b) by 263 days.

(21) Appl. No.: 13/575,572

(22) PCT Filed: Jan. 28, 2011

(86) PCT No.: PCT/JP2011/051773
§ 371 (c)(1),
(2), (4) Date: Aug. 20, 2012

(87) PCT Pub. No.: WO2011/093457
PCT Pub. Date: Aug. 4, 2011

(65) Prior Publication Data
US 2012/0316533 A1    Dec. 13, 2012

(30) Foreign Application Priority Data

Jan. 29, 2010 (JP) ................. 2010-018992

(51) Int. Cl.
*A61F 13/15* (2006.01)
*A61F 13/56* (2006.01)
*A61F 13/551* (2006.01)
*A61F 13/472* (2006.01)

(52) U.S. Cl.
CPC ......... *A61F 13/5616* (2013.01); *A61F 13/5513* (2013.01); *A61F 13/47245* (2013.01); *A61F 13/551* (2013.01); *A61F 13/5611* (2013.01); *A61F 13/5514* (2013.01)
USPC ................. 604/385.02; 604/385.04

(58) Field of Classification Search
CPC .............. A61F 13/476; A61F 13/5513; A61F 13/55135; A61F 13/5514; A61F 13/5605; A61F 13/5611; A61F 13/5616
USPC .......................... 604/385.02, 385.04, 385.201
See application file for complete search history.

(56) References Cited

U.S. PATENT DOCUMENTS

| | | | |
|---|---|---|---|
| 5,683,377 A | | 11/1997 | Mizutani |
| 5,785,698 A | * | 7/1998 | Van Iten .................. 604/387 |
| 5,868,727 A | | 2/1999 | Barr et al. |
| 6,387,084 B1 | * | 5/2002 | VanGompel et al. .... 604/385.04 |
| 6,902,552 B2 | * | 6/2005 | VanGompel et al. .... 604/385.04 |
| 7,063,689 B2 | * | 6/2006 | VanGompel et al. .... 604/385.04 |
| 7,163,529 B2 | * | 1/2007 | Mocadlo ................. 604/385.04 |
| 2003/0036740 A1 | * | 2/2003 | Hammonds et al. ..... 604/385.04 |
| 2004/0133179 A1 | * | 7/2004 | Steger et al. ............ 604/385.04 |
| 2004/0236298 A1 | * | 11/2004 | Coates .................... 604/385.04 |

FOREIGN PATENT DOCUMENTS

| | | |
|---|---|---|
| JP | 9-000567 | 1/1997 |
| JP | 9-094267 | 4/1997 |
| JP | 9-234218 | 9/1997 |
| JP | 11-504846 | 5/1999 |

(Continued)

*Primary Examiner* — Lynne Anderson
(74) *Attorney, Agent, or Firm* — Jordan and Hamburg LLP

(57) ABSTRACT

In a conveniently usable individually packaged absorbent article such as a sanitary napkin fixing adhesive layers formed on wing-shaped flaps are covered with a wing release material extended in the width direction, the wing-shaped flaps are folded to a permeable front-surface sheet side with the wing release material, a packaging material is fixed at least to the wing release material, and the wing release material and the packaging material are fixed by a first fixing region that includes portions around folding lines of the wing-shaped flaps and is formed over the forward end positions (forward-side root positions) of the folding lines of the wing-shaped flaps in the longitudinal direction.

6 Claims, 15 Drawing Sheets

(56) References Cited

FOREIGN PATENT DOCUMENTS

| JP | 3163233 | 5/2001 |
| JP | 2004-113590 | 4/2004 |
| JP | 2008-136566 | 6/2008 |

* cited by examiner

ABSORBENT ARTICLE

BACKGROUND OF THE INVENTION

The present invention relates to an absorbent article including wing-shaped flaps wrapped around the crotch of an undergarment when fixed to the undergarment.

For example, as shown in FIGS. 15 and 16, a conventional absorptive article N, e.g., a sanitary napkin, a pantiliner, a pad for vaginal discharge, and an incontinence pad is known. The absorptive article N contains an absorbing body 52 made of a cotton-state pulp between an impermeable back-surface sheet 50 such as a polyethylene sheet and a polyethylene laminate unwoven cloth and a permeable front-surface sheet 51 such as a nonwoven cloth and a permeable plastic sheet.

In order to fix the absorbent article N of this type in an attached state, the absorbent article N includes at least one adhesive layer 53 formed on, for example, the skin non-contact surface (outer surface) of the absorbent article N, wing-shaped flaps W integrally formed on both sides of a napkin body in the longitudinal direction so as to extend to the outside, and adhesive layers 54 provided on the surface of the impermeable back-surface sheet 50 side of the wing-shaped flaps W (outer surfaces).

When the absorbent article N is fixed to an undergarment 30, as illustrated in FIG. 17, the absorbent article N is fit to the crotch of the undergarment. The laterally extending wing-shaped flaps W are drawn from the undergarment. The wing-shaped flaps W are folded at folding lines RL and then are bonded to the outer surface of the crotch of the undergarment 30 to wrap around the crotch of the undergarment.

For individual packaging of the absorbent articles N, the absorbent article N may be packed in a first pattern (see Japanese Patent Laid Open No. 9-94267) in which the wing-shaped flaps W are folded to the unused surface (back surface) of the absorbent article N (hereinafter, may be simply called backward folding) or the absorbent article N may be packed in a second pattern (see Japanese Patent No. 3163233) as shown in FIG. 18 in which the wing-shaped flaps W are folded to the use surface (front side) of the absorbent article N (hereinafter, may be simply called front folding) so as to cover the respective adhesive layers 54 and the wing-shaped flaps W are connected through release paper 56 extending over the adhesive layers 54.

In the individual packaging of the first pattern, however, when a package is opened and the release paper is removed to attach the absorbent article N to the undergarment, the wing-shaped flaps W need to be unfolded by hand because the wing-shaped flaps W have been folded to the back side. In some cases, the adhesive layers 54 of the wing-shaped flaps W may be bonded to the back sheet 50 of the body and thus the peeling of the adhesive layers 54 may stretch or break the base material of the back sheet 50 of the body, so that the napkin may become unusable.

In the individual packaging of the second pattern, the wing-shaped flaps W have been folded to the use surface and thus the adhesive layers 54 formed on the wing-shaped flaps W are not bonded to the adhesive layers 53 formed on the back surface of the body. However, the release paper 56 extended over the wing-shaped flaps W needs to be separately peeled off and discarded by hand, so that one-step opening (release paper is automatically removed by a single opening operation) is not achieved. Even when the release paper 56 is peeled off, the wing-shaped flaps W are not automatically unfolded and remain folded to the front surface side by the folding line. Thus, a user needs to unfold the wing-shaped flaps W by hand upon attachment, requiring a long time for attachment.

To address this problem, the present applicant has proposed a napkin in Japanese Patent Laid Open No. 2004-113590. As illustrated in FIG. 19, the napkin in a packaged state includes a wing release material 59 covering the fixing adhesive layers 54 formed on the wing-shaped flaps W. The wing-shaped flaps W are folded to the permeable front-surface sheet side along with the wing release material 59, the wing release material 59 is extended to the surface of the impermeable back-surface sheet 50 over the folding line positions of the wing-shaped flaps W, and the wing release material 59 on the surface of the impermeable back-surface sheet 50 is fixed to a packaging material directly or through a body release material covering the fixing adhesive layers. In a state in which the wing-shaped flaps W are folded to the permeable front-surface sheet side along with the wing release material 59, the ends of the wing-shaped flaps W overlap each other so as to temporarily fix the wing-shaped flaps W to each other. Furthermore, the present inventor has proposed a napkin in Japanese Patent Laid Open No. 2008-136566 in which the adhesive strength of a wing-temporarily-fixing adhesive layer that joins the wing-shaped flaps is set lower than that of the wing-fixing adhesive layer and the wing release material.

SUMMARY OF INVENTION

According to the napkin of Japanese Patent Laid Open No. 2004-113590, the wing-shaped flaps being unfolded do not adhere to the adhesive layers formed on the back surface of the body of the napkin and one-step opening can be achieved. When the packaging material is peeled off, the wing-shaped flaps are automatically unfolded, enabling a shorter attachment time. Since the wing-shaped flaps are temporarily fixed to each other, the wing-shaped flaps can be stably kept in front folded position in the manufacturing process and flutters of the wing-shaped flaps can be eliminated in a conveyor line, achieving a stable operation.

According to the napkin of Japanese Patent Laid Open No. 2008-136566, when the packaging material being unfolded is peeled off from the napkin with the release material, the wing release material can be smoothly unfolded with the wing-shaped flaps and can be easily peeled off from the napkin.

In conventional napkins, for example, the napkins described in Japanese Patent Laid Open No. 2004-113590 and Japanese Patent Laid Open No. 2008-136566, as shown in FIG. 19, a packaging material 58 and the wing release material 59 are fixed to each other in a square fixing region 57 formed at a central part of the wing release material 59. Thus, as shown in FIGS. 20 and 21, when the packaging material 58 is peeled off, a tensile force is applied only to the central part of the wing release material 59 on which the fixing region 57 is formed. The tensile force is applied to the central part so as to draw the wing release material 59 to the outside, thereby unfolding the wing-shaped flaps to the outside. Hence, a large resistance is applied to the folding part of the wing release material 56. The large resistance may catch the wing release material 56 and interfere with smooth unfolding of the wings.

A main object of the present invention is to smoothly unfold a wing release material with wing-shaped flaps and allow a release material to be easily peeled off from an absorbent article when a packaging material being unfolded is peeled off from a napkin with the release material; the absorbent article including the wing-shaped flaps forwardly folded in a packaged state.

In order to solve the problem, an invention according to a first aspect provides an absorbent article including wing-shaped flaps formed on the respective sides of a body including an absorbing body between a permeable front-surface sheet and an impermeable back-surface sheet, the wing-shaped flaps being fixed so as to wrap around the crotch of an undergarment upon attachment, the absorbent article including: body-fixing adhesive layers formed, beside the impermeable back-surface sheet, on the surface of the impermeable back-surface sheet side of the body; and wing-fixing adhesive layers formed on the surfaces of the impermeable back-surface sheet side of the wing-shaped flaps, wherein in a packaged state, the body-fixing adhesive layers are covered with a body release material, and the fixing adhesive layers formed on the wing-shaped flaps are covered with a wing release material extended in the width direction, the wing-shaped flaps are folded to the permeable front-surface sheet side with the wing release material, a packaging material is fixed at least to the wing release material, the ends of the wing-shaped flaps verlap on the permeable front-surface sheet side, the overlapping ends of the wing-shaped flaps are directly joined to each other with a wing-temporarily-fixing adhesive layer or indirectly joined through the wing release material so as to be peeled off, and the wing release material and the packaging material are fixed by a first fixing region that contains portions around the folding lines of the wing-shaped flaps and is formed over the front end positions of the folding lines of the wing-shaped flaps in the longitudinal direction.

In the invention according to the first aspect, when the packaging material is peeled off, the wing-shaped flaps are pulled to the back-surface sheet side by the wing release material, so that the wing-shaped flaps having been folded to the front-side sheet side are automatically unfolded. At this point, the first fixing region for fixing the wing release material and the packaging material is formed at a location including the portions around the folding lines of the wing-shaped flaps on both sides and is formed over the forward end positions (forward-side root positions) of the folding lines of the wing-shaped flaps in the longitudinal direction. Thus, the forward end of the wing release material is peeled to the outside substantially over the length between the folding lines on both sides before the packaging material is peeled to the forward-side root positions of the wing-shaped flaps. After that, when the packaging material is peeled to the front-side root positions of the wing-shaped flaps, the wing release material covering the wing-shaped flaps is also peeled to the outside, allowing the wing-shaped flaps to be simultaneously unfolded to both sides with respect to positions near the folding lines. Therefore, the wing release material can be smoothly unfolded with the wing-shaped flaps and the release material can be easily peeled off from the absorbent article.

As an invention according to a second aspect, the absorbent article according to the first aspect is provided, wherein the first fixing region is formed to include the vicinity located inside the folding lines of the wing-shaped flaps, within 10 mm from the folding lines.

The invention according to the second aspect specifies the range of the first fixing region that includes the vicinity inside the folding lines of the wing-shaped flaps, within 10 mm from the folding lines. Thus, the tensile force of the wing release material can be more reliably converted to a force in the direction of unfolding the wing-shaped flaps.

As an invention according to a third aspect, the absorbent article according to any one of the first and second aspects is provided, wherein the first fixing region is continuously formed in a section including the portions around the folding lines in the width direction of the absorbent article, or the first fixing region is formed to be separated into at least two regions including at least both sides of the section.

The invention of the third aspect specifies the formation patterns of the first fixing region. The first fixing region is continuously formed in the section including the portions around the folding lines in the width direction, or the first fixing region is formed to be separated into at least two regions including at least both sides of the section. In the case where the first fixing region is continuously formed across the width in the section, a tensile force can be evenly applied to the wing release material. On the other hand in the case where the first fixing region is formed separately in the section, at least two regions including at least both sides of the section are formed, thereby saving materials such as an adhesive while securing a tensile force on the portions around the folding lines.

As an invention according to a fourth aspect, the absorbent article according to any one of the first to third aspects is provided, wherein the wing-fixing adhesive layer is shifted to the rear side of the wing-shaped flap, and the wing-fixing adhesive layer is formed with a clearance of at least 30 mm from the front end position of the folding line to the rear side of the wing-shaped flap.

In the invention according to the fourth aspect, in order to sufficiently apply a force for unfolding the wing-shaped flaps by a tensile force from the wing release material, the wing-fixing adhesive layers are shifted to the rear sides of the wing-shaped flaps such that the wing-fixing adhesive layers and the wing release material are not separated from each other before the wing-shaped flaps are unfolded. The amount of the shift is preferably a clearance of at least 30 mm from the front end position of the folding line to the rear side of the wind-shaped flap.

When the wing-shaped flaps are unfolded, as shown in FIG. 4, the wing-shaped flap is subjected to a component force $T_H$ that pulls the wing-shaped flap to the outside in the width direction in the plane of the wing-shaped flap and a component force $T_V$ that pulls the wing-shaped flap to the front side in the plane of the wing-shaped flap, with respect to a force T whose base point lies on a front-side root position P. Since the wing-fixing adhesive layer is formed with a clearance of at least 30 mm from the front-side root position to the rear side of the wing-shaped flap, the forward component tensile force $T_V$ is larger than the outward component tensile force $T_H$. This allows the forward component tensile force $T_V$ to act as a force separating the wing-shaped flaps from the surface of the absorbent article, so that the wing-shaped flaps can be more smoothly unfolded.

As an invention according to a fifth aspect, the absorbent article according to any one of the first to fourth aspects is provided, wherein a second fixing region is formed in which the forward end of the body release material is extended forward of the wing release material, the second fixing region being formed across the body release material and the wing release material to fix the body release material, the wing release material, and the packaging material.

In the invention according to the fifth aspect, the second fixing region for fixing the body release material, the wing release material, and the packaging material is formed. Thus, the body release material can be peeled sequentially from the front end, facilitating smooth peeling. Furthermore since the second fixing region is formed across the body release material and the wing release material, the joining state of the body release material, the wing release material, and the packaging material can be reliably maintained in a manufacturing process of the absorbent article, thereby preventing wrinkles and bending on the release materials and the packaging material.

As an invention according to a sixth aspect, the absorbent article according to any one of the first to fifth aspects is provided, wherein a wing-temporarily-fixing adhesive layer joining the wing-shaped flaps has an adhesive strength lower than the adhesive strength of the wing-fixing adhesive layer and the wing release material.

In the invention according to the sixth aspect, the adhesive strength of the wing-temporarily-fixing adhesive layer is set lower than that of the wing-fixing adhesive layer and the wing release material. Thus, the wing-shaped flaps can be easily released from temporary fixation, allowing the wing release material to be smoothly unfolded.

As specifically described above, the present invention makes it possible to smoothly unfold a wing release material with wing-shaped flaps and allow a release material to be easily peeled off from an absorbent article when a packaging material being unfolded is peeled off from a napkin with the release material, the absorbent article including the wing-shaped flaps front-folded in a packaged state.

DETAILED DESCRIPTION OF THE INVENTION

An embodiment of the present invention will be specifically described below with reference to the accompanying drawings.

(Basic Structure of a Sanitary Napkin 1)

Figure 1:
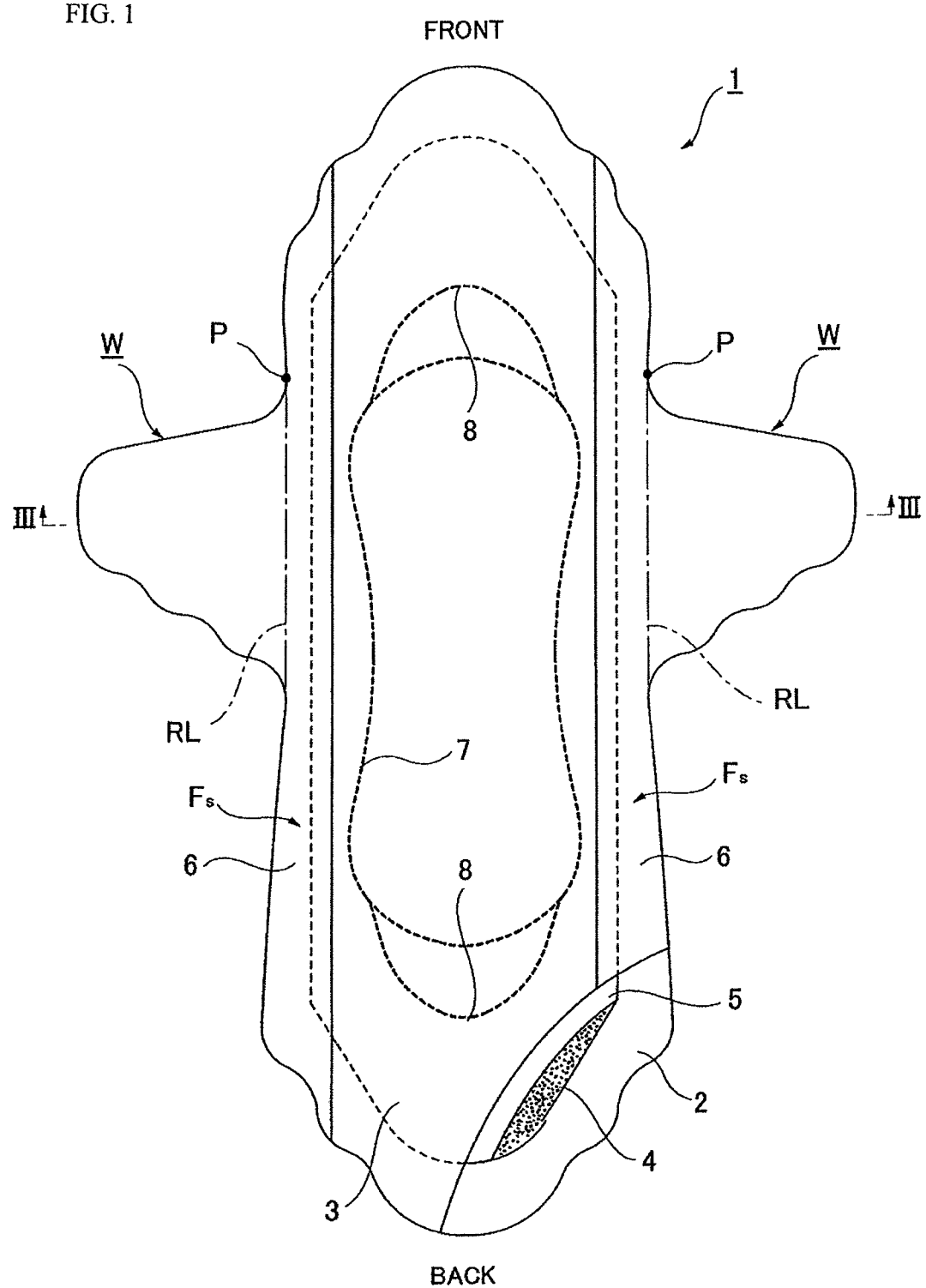
FIG. 1 is a partial cutaway development illustrating a sanitary napkin 1 according to the present invention.
Figure 2:
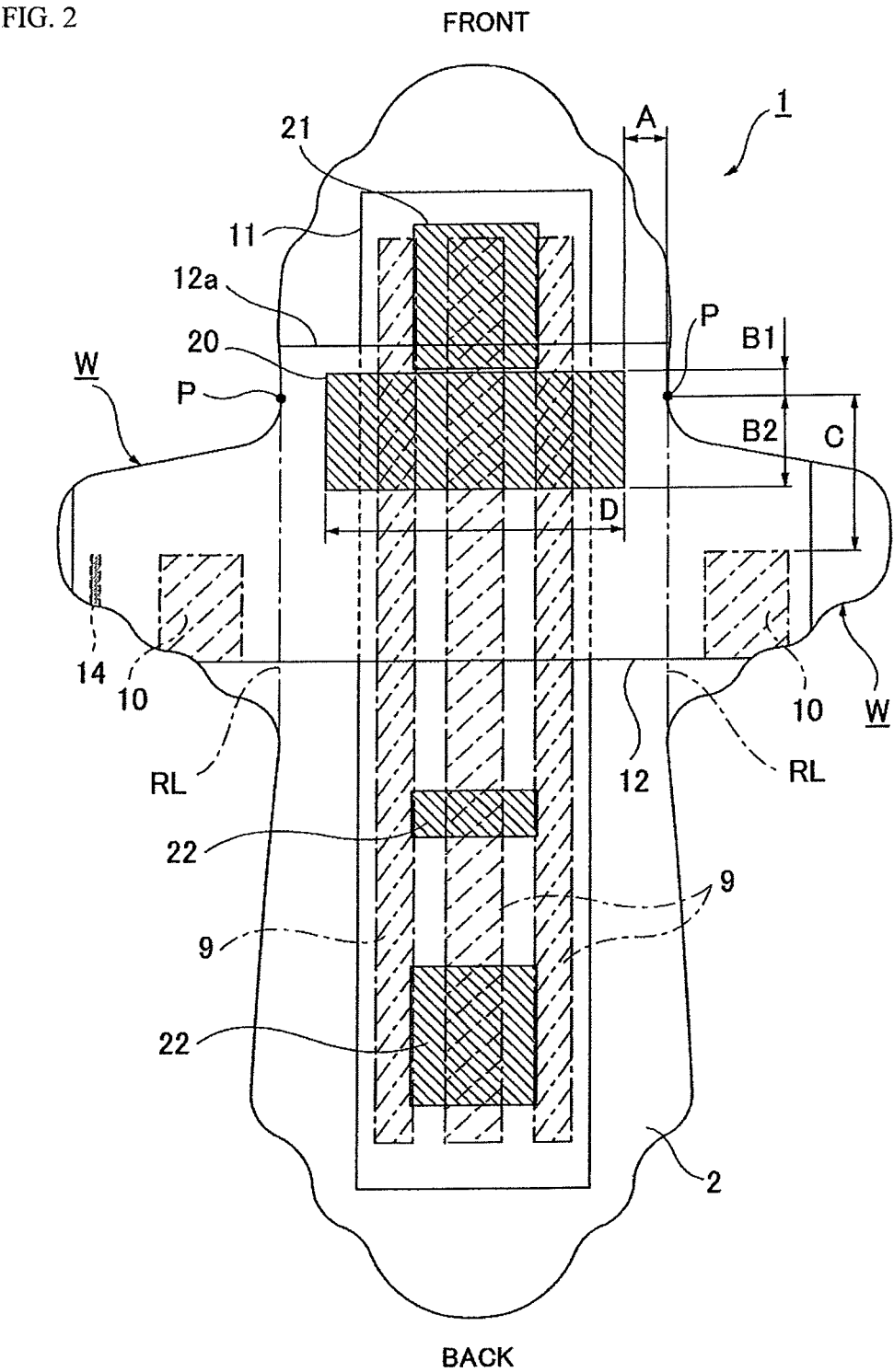
FIG. 2 is a rear view of FIG. 1.
Figure 3:
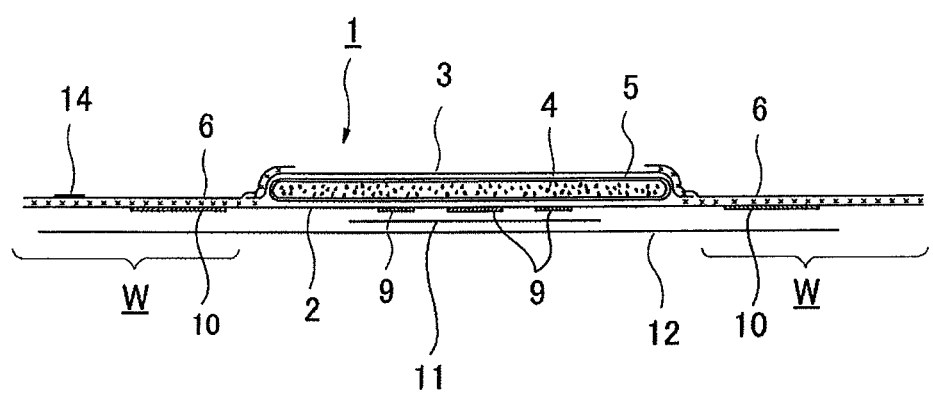
FIG. 3 is an arrow view taken along line III-III of FIG. 1.

The sanitary napkin 1 according to the present invention includes, as illustrated in FIGS. 1 to 3, an impermeable back-surface sheet 2 composed of sheets such as a polyethylene sheet and a polypropylene sheet, a permeable front-surface sheet 3 which allows quick permeation of menstrual blood, vaginal discharge, and so on, an absorbing body 4 made of a cotton pulp or synthetic pulp interposed between the sheets 2 and 3, crepe paper 5 that surrounds the absorbing body 4 to keep the shape of the absorbing body 4 and improve dispersion, and side unwoven cloths 6 formed in the longitudinal direction on both sides of the front surface. On the periphery of the absorbing body 4, the outer edges of the impermeable back-surface sheet 2 and the permeable front-surface sheet 3 on the upper and lower edges of the absorbing body 4 are joined with an adhesive such as hot-melt or by bonding means such as heat seal. Moreover, on the side edges of the absorbing body 4, the impermeable back-surface sheet 2 and the side unwoven cloths 6, which laterally extend out of the absorbing body 4, are joined with an adhesive such as hot-melt or by bonding means such as heat seal. In the present specification, flap portions on the side edges will be referred to as "circumferential side flaps $F_S$".

A structure of the sanitary napkin 1 will be further described below in detail.

A sheet material having at least water shielding performance, e.g., a sheet of olefin resins such as polyethylene and polypropylene is used for the impermeable back-surface sheet 2. Moreover, a laminate unwoven cloth is usable in which an unwoven cloth is laminated on a polyethylene sheet or the like, or an unwoven cloth sheet including a water-proof film to substantially ensure impermeability is usable (in this case, the impermeable back-surface sheet is composed of a water-proof film and a unwoven cloth). In recent years, the trend has shifted to sheets having moisture permeability from the viewpoint of prevention of sticky feeling. The water-shielding/moisture permeable sheet material is a micro-porous sheet obtained by melting and kneading an inorganic filler in an olefin resin, e.g., polyethylene or polypropylene, molding a sheet, and then stretching the sheet in an uniaxial or biaxial direction.

Subsequently, a porous or non-porous unwoven cloth or a porous plastic sheet is preferably used for the permeable front-surface sheet 3. Material fibers constituting the unwoven cloth may be synthetic fibers including olefins such as polyethylene and polypropylene, polyesters, and polyamide, recycled fibers such as rayon and supra, and natural fibers such as cotton. Furthermore, an unwoven cloth obtained by appropriate processing methods such as spunrace method, spun-bond method, thermal bond method, melt-blown method, and needle punch method can be used. Among these processing methods, the spunrace method is advantageous in its high flexibility and excellent drape property while the thermal bond method is advantageous in its bulkiness and softness.

On the top surface of the permeable front-surface sheet 3, a gourd-shaped circular emboss 7 is formed that surrounds a blood discharge part. Moreover, arc-shaped embosses 8 are formed at the forward and rear of the circular emboss 7.

The absorbing body 4 interposed between the impermeable back-surface sheet 2 and the permeable front-surface sheet 3 is composed of, for example, fluff pulp and a water-absorbing polymer. The water-absorbing polymer is mixed as, for example, granular powder in the pulp constituting the absorbing body. The pulp includes chemical pulp obtained from lumber, cellulose fibers such as molten pulp, and artificial cellulose fibers such as rayon and acetate. Softwood pulp with a fiber length longer than that of hardwood pulp is preferably used in terms of functions and price. The provision of the crepe paper 5 surrounding the absorbing body 4 in the present example interposes the crepe paper 5 between the permeable front-surface sheet 3 and the absorbing body 4. The crepe paper 5 having high absorbency quickly diffuses a body fluid and prevents backflow of menstrual blood or the like.

The side unwoven cloths 6 are provided on both sides of the front surface of this sanitary napkin 1 in the longitudinal direction substantially over the length of the napkin 1. The side unwoven cloths 6 are partially extended in a lateral direction and form wing-shaped flaps W with a part of the impermeable back-surface sheet 2 that is similarly extended in the lateral direction.

For the side unwoven cloth 6, a water-repellent treated unwoven cloth or hydrophilically treated unwoven cloth can be used from the viewpoint of a function to be emphasized. For example, if an emphasis is to be placed on a function to prevent permeation of menstrual blood and vaginal discharge or the like or a function to improve a texture, a water-repellent treated unwoven cloth coated with silicon, paraffin, alkyl chromic chloride water-repellent is desirably used. If an emphasis is placed on absorbency of menstrual blood or the like in the wing-shaped flaps W, it is desirable to use a hydrophilically treated unwoven cloth provided with a hydrophilic property by applying a capillary phenomenon. In the hydrophilically treated unwoven cloth, the synthetic fibers are made swollen or porous by using a method of polymerization through coexistence of a compound having a hydrophilic group such as an oxidized product of polyethylene glycol, for example, in a manufacture process of the synthetic fibers, and a method of precipitating a hydroxide of metal through treatment with metal salts such as stannic chloride and partial melting that forms a porous surface.

As shown in FIG. 2, on the skin non-contact surface of the body including the absorbing body 4 between the permeable front-surface sheet 3 and the impermeable back-surface sheet 2, a plurality of body-fixing adhesive layers 9 are formed in a proper application pattern to fix the napkin 1 to a undergarment. In FIG. 2, the three body-fixing adhesive layers 9 are formed. Moreover, the body-fixing adhesive layers 9 are covered with a body release material 11. On the surfaces of the impermeable back-surface sheet 2 side of the wing-shaped flaps W, wing-fixing adhesive layers 10 are formed. The wing-fixing adhesive layers 10 are covered with one wing release material 12 that is extended in the width direction. The wing release material 12 is extended to a predetermined position located forward of the wing-shaped flaps W and has an outer periphery cut along the edge of the body of the napkin. The body release material 11 and the wing release material 12 are fixed to a packaging sheet 16 respectively, which will be described later.

Adhesives mainly composed of, for example, any one of styrenic polymers, tackifiers, and plasticizers are preferably used for forming the fixing adhesive layers 9 and 10. The styrenic polymers include a styrene-ethylene-bytylene-styrene block copolymer, a styrene-butylene-styrene block copolymer, and a styrene-isobutylene-styrene block copolymer. One of the copolymers may be used or a polymer blend of at least two of the copolymers may be used. Among these copolymers, styrene-ethylene-bytylene-styrene block copolymer is preferable because of its high thermal stability. The tackifiers and plasticizers are preferably solid at room temperature. The tackifiers include, for example, C5 petroleum resin, C9 petroleum resin, dicyclopentadiene petroleum resin, rosin petroleum resin, polyterpene resin, and terpene phenol resin. The plasticizers include, for example, monomer plasticizers such as triphenyl phosphate, dibutyl phthalate, and dioctyl phthalate, and polymer plasticizers such as vinyl polymers and polyester.

The release materials 11 and 12 may be sheets of paper or plastic sheets prepared by applying or spraying mold release agents such as silicone resin, fluorine-based resin, and tetrafluoroethylene resin on the contact surfaces of the fixing adhesive layers 9 and 10, and releasing the sheets. In this case, at least for the wing release material 12, a plastic sheet with high flexibility is preferably used to smoothly unfold the wing flaps W when the package is opened and the packaging material is peeled off. Films or nonwoven cloths may be used without any special releasing operations as long as the adhesion does not substantially decrease.

Figure 4:
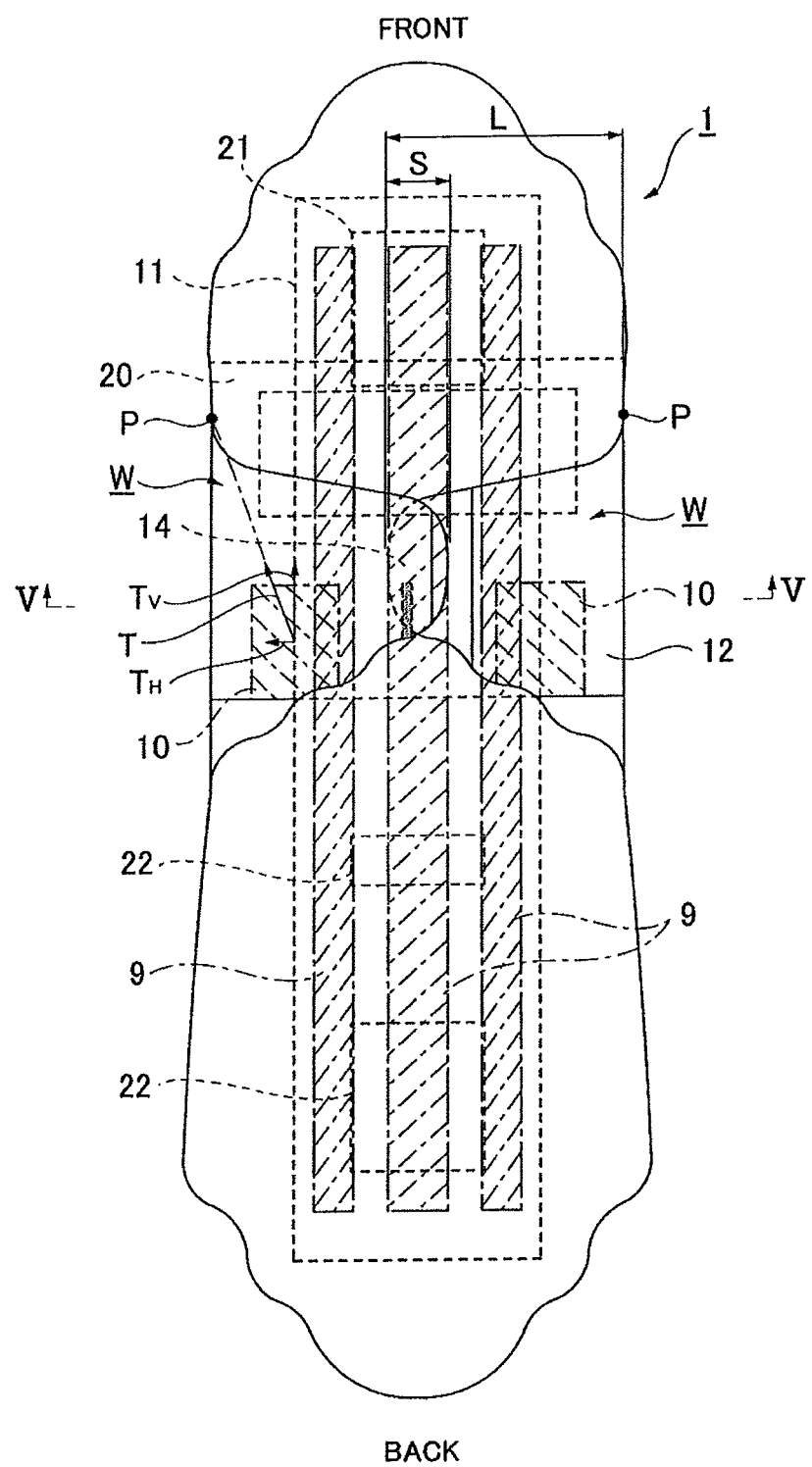
FIG. 4 is a plan view illustrating a folding procedure of wing-shaped flaps.
Figure 5:
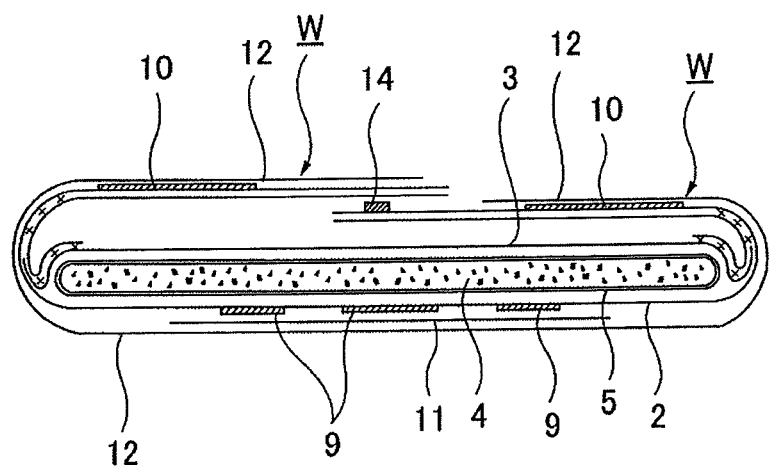
FIG. 5 is a transverse section of FIG. 4 (cross-sectional view taken along line V-V of FIG. 4).

In the packaging of the sanitary napkin 1, as shown in FIG. 4, one of the wing-shaped flaps W is folded at a folding line RL (see FIGS. 1 and 2), which is set at a position connecting the wing-shaped flap W to a circumferential side flap $F_S$ of the body, to the permeable front-surface sheet 3 side along with the wing release material 12, and then the other wing-shaped flap W is folded at a folding line RL (see FIGS. 1 and 2), which is set at a position connecting the wing-shaped flap W to a circumferential side flap $F_S$ of the body, to the permeable front-surface sheet 3 side along with the wing release material 12.

In this case, the wing-shaped flaps W simply folded to the permeable front-surface sheet 3 may not be stable in shape. Thus, the wing-shaped flaps W may protrude or flutter, leading to improper positioning or entanglement in a conveyor line. Thus, the wing-shaped flaps W are kept in a state of being folded to the permeable front-surface sheet 3 side with the wing release material 12 to stabilize an operation. Specifically, the ends of the wing-shaped flaps W folded to the permeable front-surface sheet 3 side are caused to overlap each other, and as shown in FIG. 4, the wing-shaped flaps W on the overlapping portion are directly bonded to each other and are temporarily fixed with a wing-temporarily-fixing adhesive layer 14 provided on the back side (or the front side) of the end of one of the wing-shaped flaps W. For the temporary fixation of the wing-shaped flaps W, in the case where the wing-temporarily-fixing adhesive layer 14 is provided on the front surface of the end of the wing-shaped flap W and the wing release material 12 on the other wing-shaped flap W below the front surface of the end of the wing-shaped flap w covers the end of the wing-shaped flap W, the wing-temporarily-fixing adhesive layer 14 may be bonded to the wing release material 12 and the wing-shaped flaps W may be indirectly joined to each other through the wing release material 12. An overlap S of the wing-shaped flaps W is desirably set to at least about a quarter of a protrusion length L of the wing-shaped flap W to further stabilize the operation.

As described in Japanese Patent Laid-Open No. 2008-136566, in the napkin 1, the adhesive strength of the wing-temporarily-fixing adhesive layer 14 that joins the wing-shaped flaps W is set lower than that of the wing-fixing adhesive layer 10 and the wing release material 12. In this case, the adhesive strength of the wing-temporarily-fixing adhesive layer 14 that joins the wing-shaped flaps is 0.05 (N) to 1.00 (N), preferably 0.05 (N) to 0.60 (N), and the adhesive strength of the wing-fixing adhesive layer 10 and the wing release material 12 is 0.15 (N) to 1.50 (N), preferably 0.25 (N) to 1.30 (N). An adhesive strength ratio calculated by the adhesive strength of the wing-temporarily-fixing adhesive layer 14 and the adhesive strength of the wing-fixing adhesive layer 10 and the wing release material 12 is desirably 0.05 to 0.80, preferably 0.05 to 0.70. In the case where the adhesion strength of the wing-temporarily-fixing adhesive layer 14 is less than 0.05 (N), the wing-shaped flaps W cannot be temporarily bonded and fixed to a sufficient level. In the case where the adhesive strength exceeds 1.00 (N), the wing-shaped flaps W cannot be easily unfolded when the release materials 11 and 12 are peeled off. In the case where the adhesive strength of the wing-fixing adhesive layer 10 and the wing release material 12 is less than 0.15 (N), improper positioning may occur when the napkin 1 is attached to an undergarment. In the case where the adhesive strength exceeds 1.50 (N), the release materials 11 and 12 are less likely to be peeled off. The adhesive strength is a numeric value obtained by a test method described in Japanese Patent Laid-Open No. 2008-136566.

After the wing-shaped flaps W are folded to the front surface side with the wing release material 12, the sanitary napkin 1 is wrapped with the packaging sheet 16.

Figure 6:
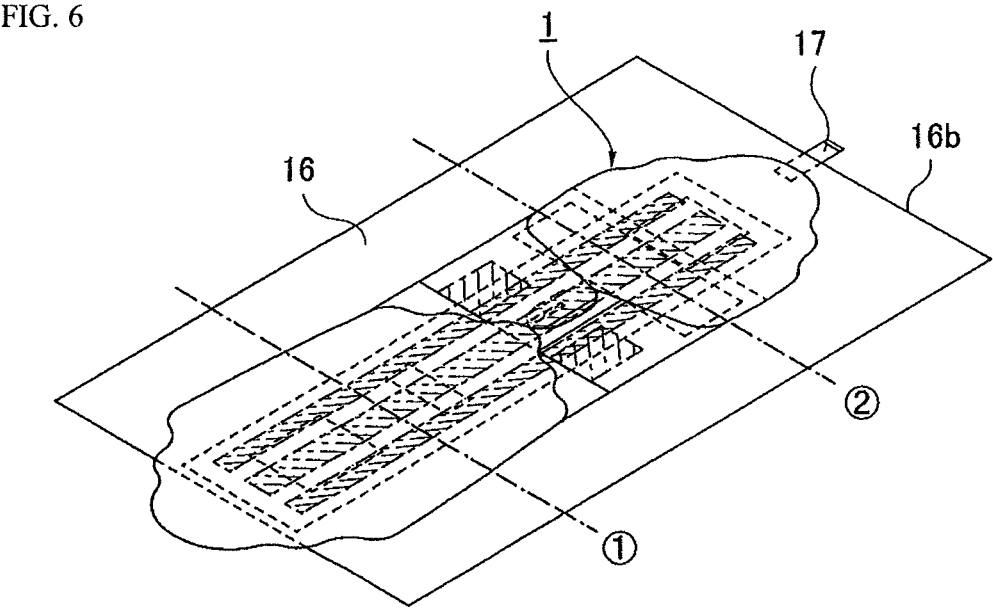
FIG. 6 is a perspective view illustrating a packaging procedure.

As shown in FIG. 6, in this packaging method, the packaging sheet 16 having a predetermined length is smaller in width than the unfolded napkin 1 (a distance between the ends of the wing-shaped flaps W) and is larger in width than the napkin 1 when the wing-shaped flaps W are folded. The napkin 1 is placed on the packaging sheet 16 such that at least one of short sides 16b of the packaging sheet 16 is located outside one of the forward and rear ends of the napkin 1, and the packaging sheet 16 and the at least wing release material 12 are firmly bonded to each other with a hot-melt adhesive or the like in a predetermined fixing region, which will be specifically discussed later. It is desirable to firmly bond the packaging sheet 16, the body release material 11, and the wing release material 12 with a hot-melt adhesive or the like.

Figure 7:
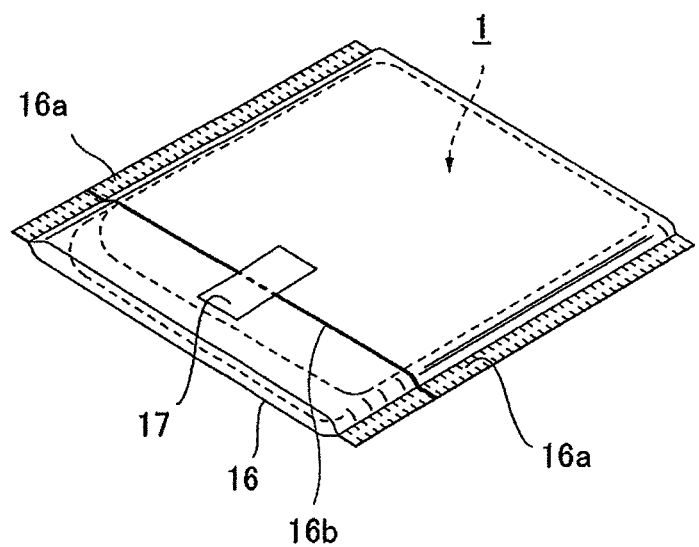
FIG. 7 is a perspective view illustrating a packaged state.

After that, the rear end of the napkin is folded at folding line (1), the forward end of the napkin is folded at folding line (2), and then as shown in FIG. 7, open side edges 16a of the packaging sheet 16 are sealed with at least one of proper sealing means including thermal embossing, heat sealing, and an adhesive. The edges 16b of the packaging sheet 16 in the longitudinal direction are bonded with an adhesive and then are preferably sealed with tub tape 17.

Figure 8:
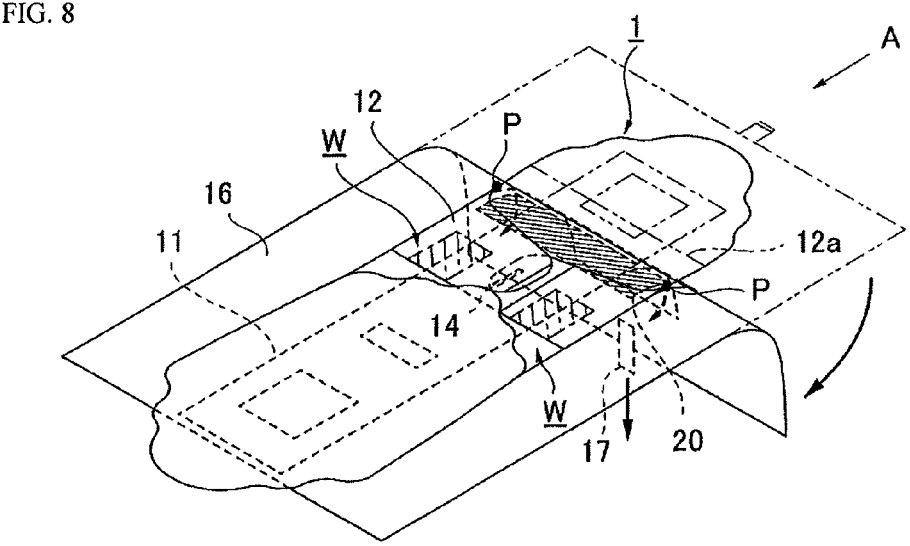
FIG. 8 is a perspective view illustrating an opening procedure (1).
Figure 9:
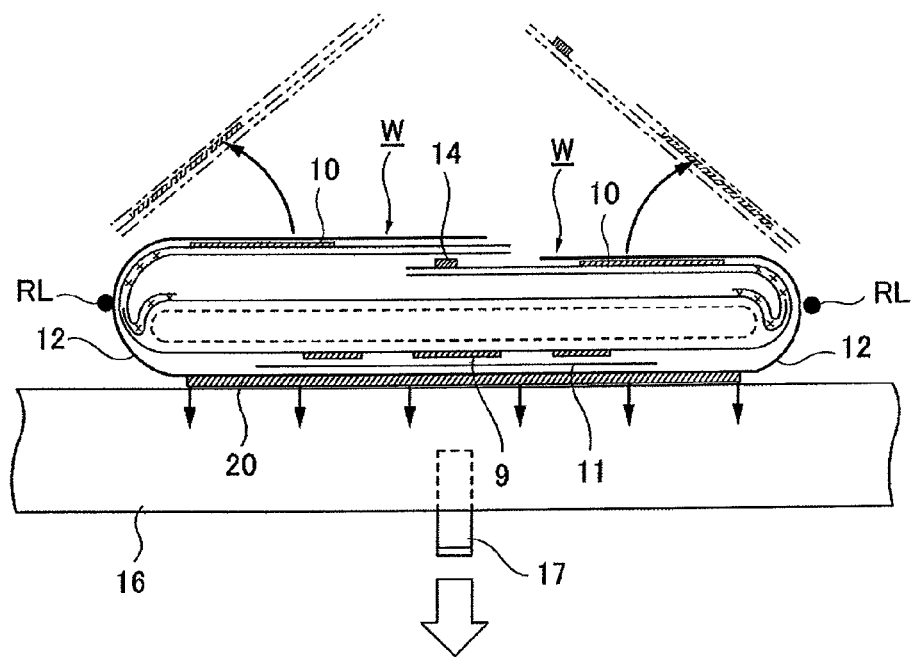
FIG. 9 is an arrow view from A of FIG. 8.
Figure 10:
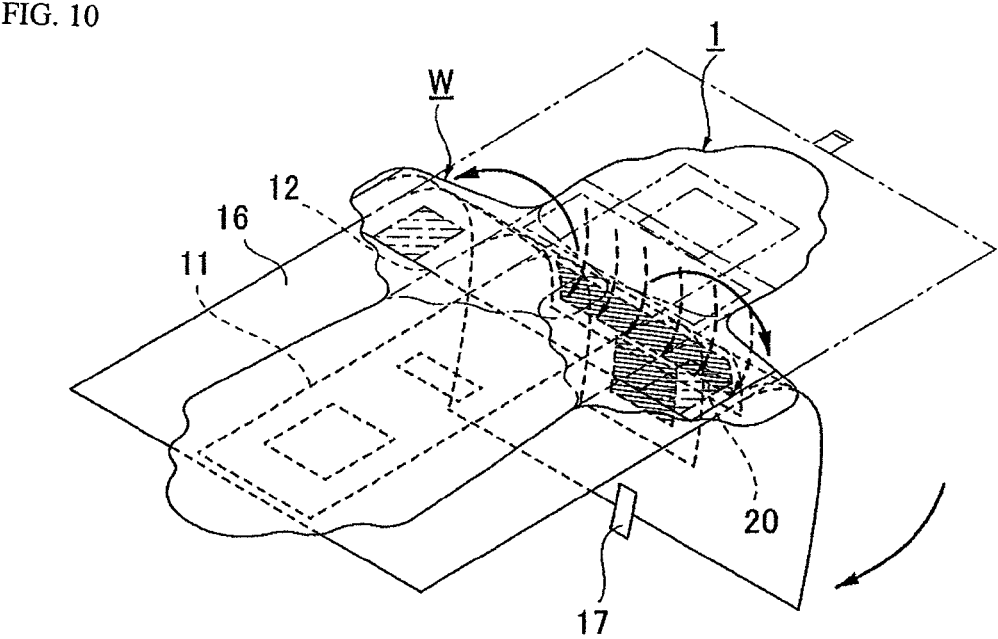
FIG. 10 is a perspective view illustrating an opening procedure (2).

In the case of the packaged absorbent article, as shown in FIGS. 8 to 10, the napkin 1 is removed from the package and the packaging sheet 16 is peeled off, so that the wing-shaped flaps W are pulled to the back surface sheet side by the wing release material 12, automatically unfolding the wing-shaped flaps W having been folded to the front surface side. At this point, the adhesive strength of the wing-temporarily-fixing adhesive layer 14 that joins the wing-shaped flaps W is set lower than that of the wing-fixing adhesive layer 10 and the wing release material 12, thereby easily releasing the temporary fixation of the wing-shaped flaps W. Moreover, the position of a forward-side line 12a of the wing release material 12 (see also FIG. 2) is shifted forward from a forward-side root position P of the wing-shaped flap W by at least 5 mm. Thus, when the body release material 11 is peeled off from the forward side of the napkin 1 and the wing-shaped flaps W are gradually unfolded from the forward side of the napkin 1, the folding lines gradually disappear from the forward of the napkin 1, thereby smoothly unfolding the wing-shaped flaps W with a smaller resistance force applied to the wing release material 12. Moreover, when the wing release material 12 is peeled off from the wing-fixing adhesive layers 10, the wing release material 12 can be easily peeled off from the wing-fixing adhesive layers 10 because the wing-shaped flaps W are gradually unfolded.

In the sate after the wing-shaped flaps w are unfolded, the unfolded wing-shaped flaps W are still somewhat slightly inclined to a use surface side with the folding lines, so that the wing-shaped flaps W do not adhere to the fixing adhesive layers 9 formed on the back surface of the body. When the packaging sheet 16 is peeled off, the body release material 11 is peeled off with the wing release material 12, achieving complete one-step opening.

(Fixing Region)

The fixing region of the packaging sheet 16, the body release material 11, and the wing release material 12 will be described below.

As shown in FIG. 2, the wing release material 12 and the packaging sheet 16 are fixed by a first fixing region 20 that includes portions around the folding lines RL of the wing-shaped flaps W on both sides and is formed over the forward end positions (hereinafter, will be also called "forward-side root positions P") of the folding lines RL of the wing-shaped flaps W in the longitudinal direction.

The formation of the first fixing region 20 allows the wing release material 12 to be smoothly unfolded with the wing-shaped flaps W when the packaging sheet 16 is peeled off to automatically unfold the wing-shaped flaps W, so that the release material can be easily peeled off from the sanitary napkin 1. To be specific, the tub tape 17 provided on the forward side edge of the packaging sheet 16 is held with one hand and the packaging sheet 16 is pulled to the outer surface of the napkin 1 while the forward end of the sanitary napkin 1 is held with the other hand, so that the forward end of the wing release material 12 is peeled off to the outside before the packaging sheet 16 is peeled to the forward-side root positions P of the wing-shaped flaps W. This is because the first fixing region 20 is formed substantially across the width between the folding lines RL on both sides and over the forward-side root positions P of the wing-shaped flaps W in the longitudinal direction. After that, when the packaging sheet 16 is peeled to the front-side root positions P of the wing-shaped flaps W, the wing release material 12 covering the wing-shaped flaps is also peeled to the outside. Thus, the wing-shaped flaps W on both sides can be simultaneously unfolded to both sides with respect to positions near the folding lines RL as a rotation center.

The first fixing region 20 is located as shown in FIG. 2 such that an inward distance A from the folding line RL of the wing-shaped flap W is 10 mm or less, preferably, 5 mm or less. With respect to the forward-side root position P as a base point, a forward-side formation length B1 of the first fixing region 20 is preferably 5 mm to 25 mm within the forward edge of the wing release material 12 and a rear formation length B2 is at least 10 mm to 20 mm within the rear edge of the wing release material 12. In the case where A is larger than 10 mm, the tensile force of the packaging sheet 16 is less likely to unfold the wing-shaped flaps W and is likely to drag the wing release material 12 to the outside.

Figure 11:
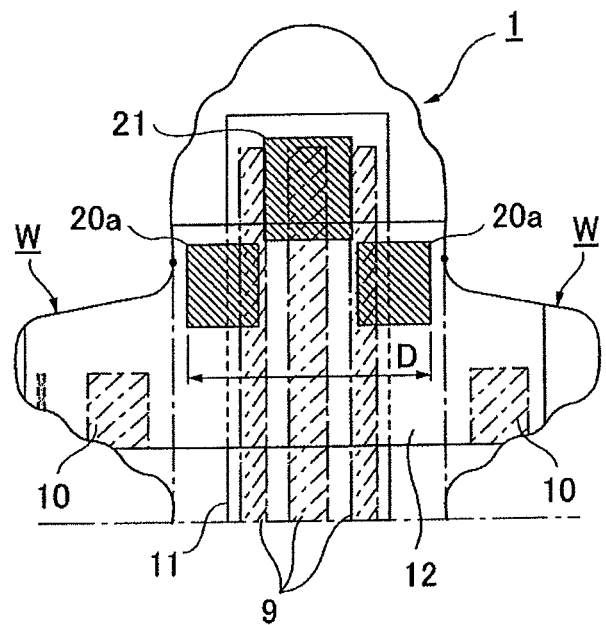
FIG. 11 is a rear view illustrating the front side of the sanitary napkin 1 according to another example (1) of a first fixing region 20.
Figure 12:
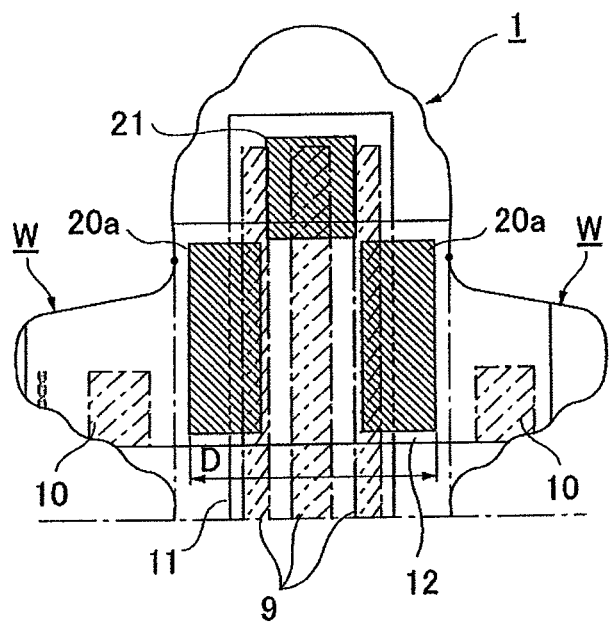
FIG. 12 is a rear view illustrating the front side of the sanitary napkin 1 according to another example (2) of the first fixing region 20.
Figure 13:
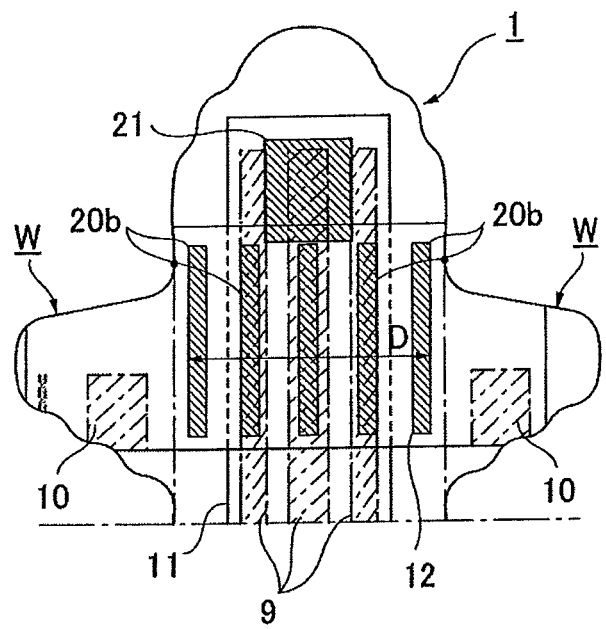
FIG. 13 is a rear view illustrating the front side of the sanitary napkin 1 according to another example (3) of the first fixing region 20.
Figure 14:
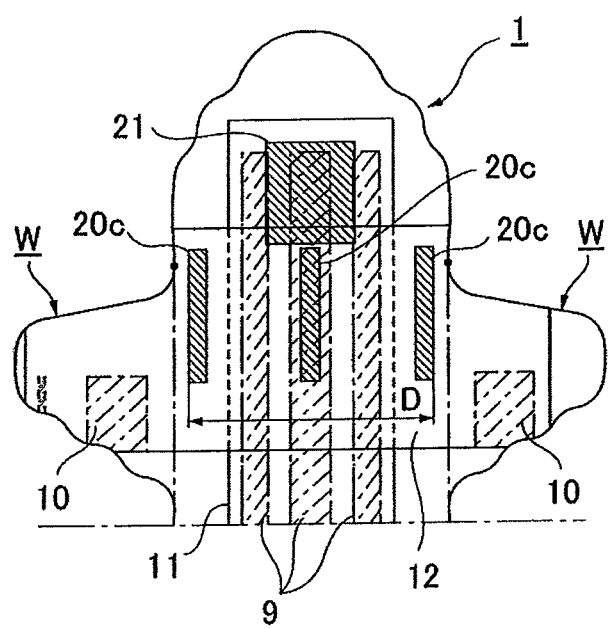
FIG. 14 is a rear view illustrating the front side of the sanitary napkin 1 according to another example (4) of the first fixing region 20.
Figure 15:
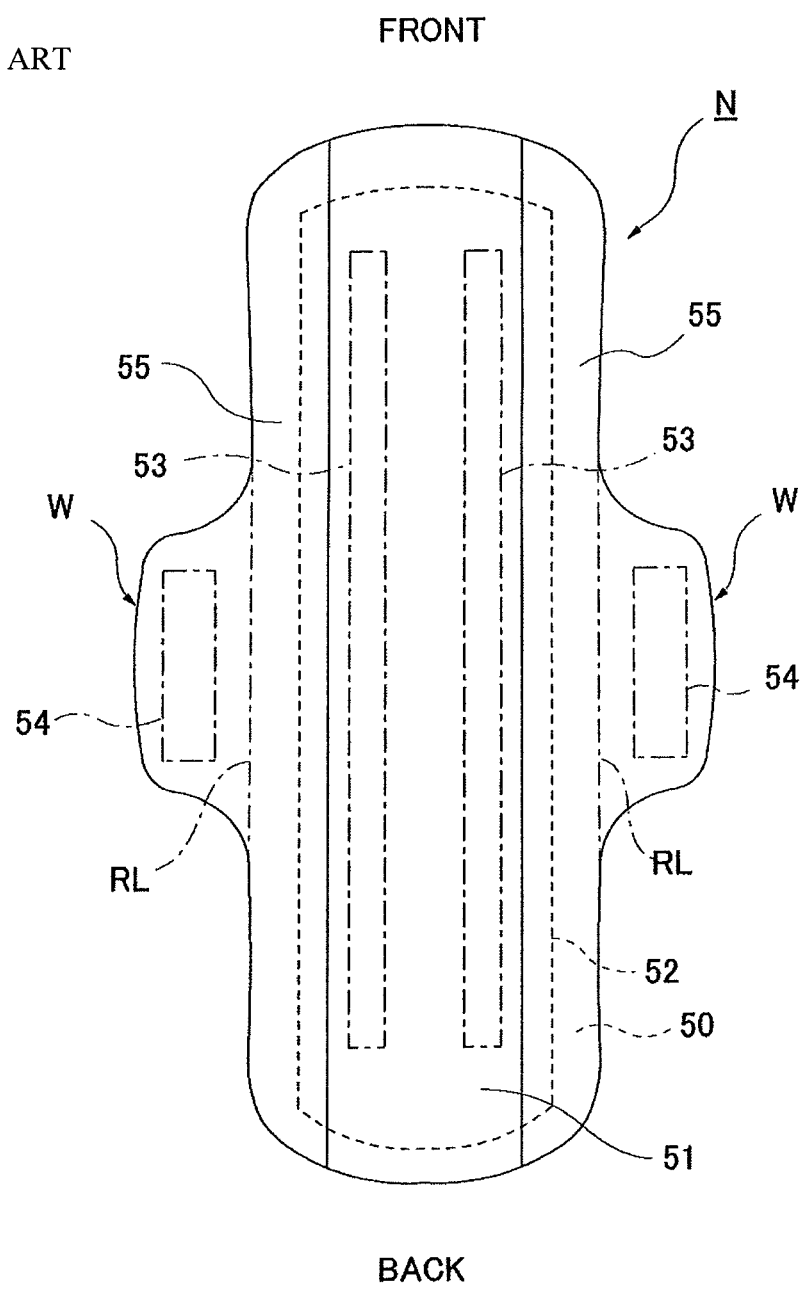
FIG. 15 is a development illustrating a conventional sanitary napkin N.
Figure 16:
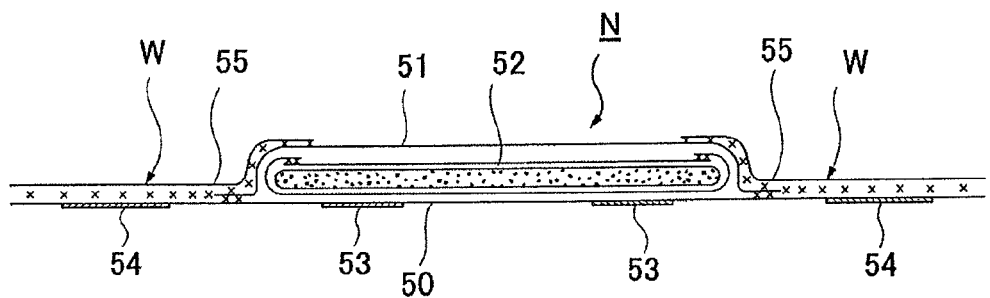
FIG. 16 is a transverse section of FIG. 15.
Figure 17:
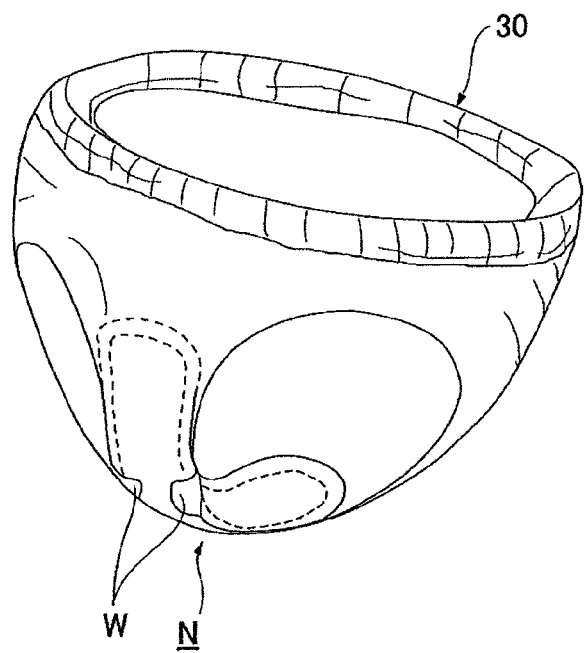
FIG. 17 illustrates a state of attachment.
Figure 18:
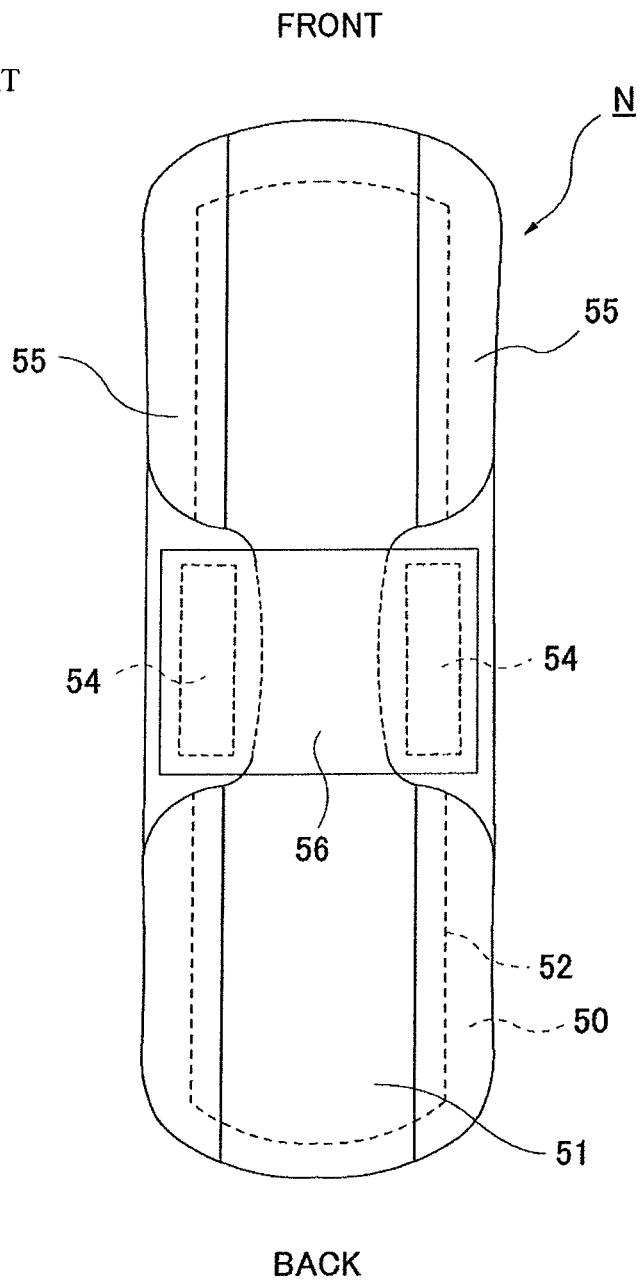
FIG. 18 is a plan view illustrating a folding procedure of conventional wing-shaped flaps W.
Figure 19:
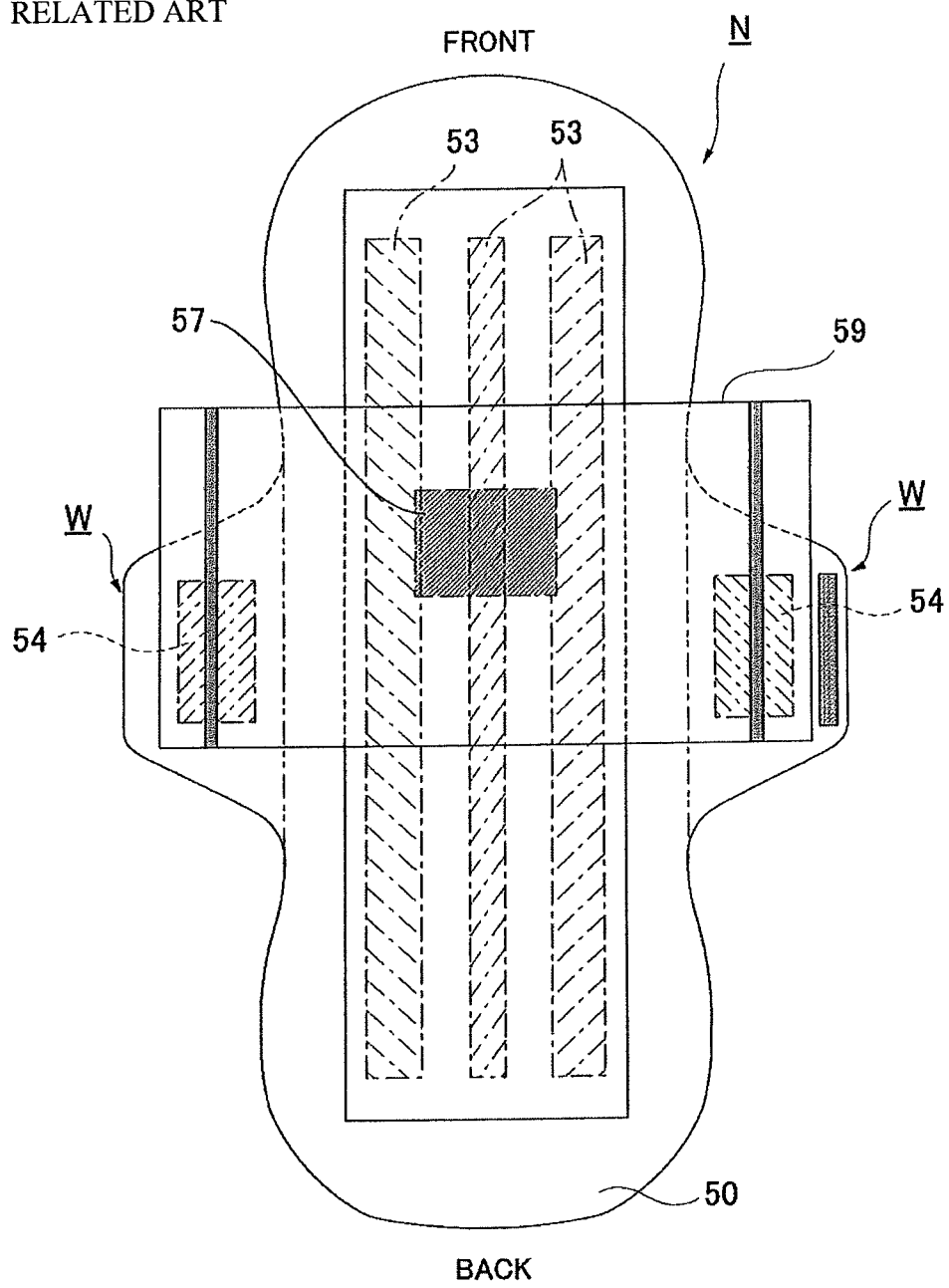
FIG. 19 is a rear view illustrating the conventional sanitary napkin N having a region fixed to a packaging material.
Figure 20:
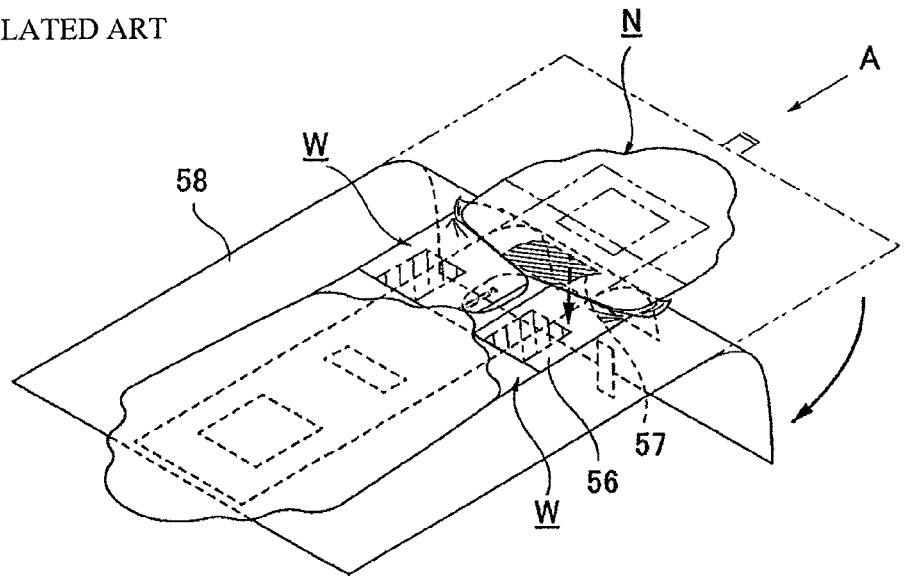
FIG. 20 is a perspective view illustrating a conventional packaging procedure.
Figure 21:
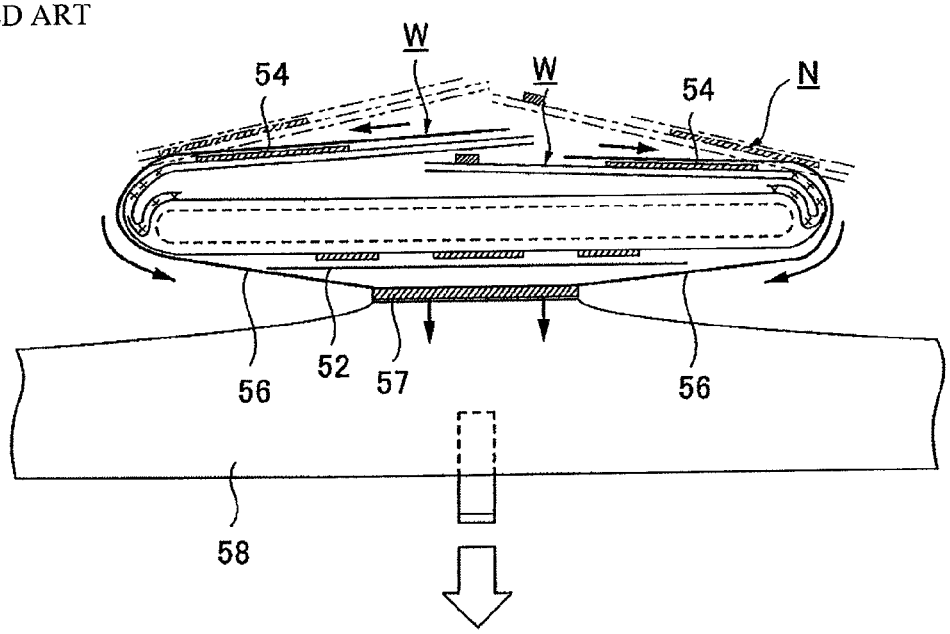
FIG. 21 is an arrow view illustrating the conventional packaging procedure, taken from A of FIG. 20.

The first fixing region 20 can be formed in various shapes as long as the first fixing region 20 includes the portions around the folding lines RL. For example, as shown in FIG. 2, the first fixing region 20 can be continuously formed in a section D that includes the portions around the folding lines RL on both sides in the width direction of the napkin 1. In this case, the tensile force of the packaging sheet 16 can be evenly applied to the wing release material 12 in the section D. As shown in FIG. 11, fixing regions 20a may be formed on both sides of the section D and no fixing region may be formed in the middle of the section D. In this case, materials such as an adhesive can be saved while bonding conditions in the portions around the folding lines RL can be secured. As shown in FIG. 12, the fixing regions 20a formed on both sides of the section D can be extended to the rear side within the rear edge of the wing release material 12. In this case, even when the wing-shaped flaps W are unfolded to both sides, the tensile force of the packaging sheet 16 can be reliably transmitted to the wing release material 12. Furthermore, as shown in FIGS. 13 and 14, the fixing regions can be separately provided in the section D. FIG. 13 shows five fixing regions 20b formed in the section D. FIG. 14 shows three fixing regions 20c formed in the section D.

As shown in FIG. 2, the wing-fixing adhesive layers 10 are shifted to the rear sides of the wing-shaped flaps W. The wing-fixing adhesive layer 10 is preferably formed with a clearance C of at least 30 mm, more preferably at least 34 mm from the front-side root position P to the rear side. This is because when the clearance C is small, the wing-fixing adhesive layers 10 may start peeling off before the wing-shaped flaps W are fully unfolded.

When the wing-shaped flaps W are unfolded, as shown in FIG. 4, the wing-shaped flap W is subjected to a component force $T_H$ that pulls the wing-shaped flap W to the outside in the width direction in the plane of the wing-shaped flap and a component force $T_V$ that pulls the wing-shaped flap W to the forward side in the plane of the wing-shaped flap W, with respect to a force T whose base point lies on the forward-side root position P. Since the wing-fixing adhesive layer 10 is formed with a clearance of at least 30 mm from the forward-side root position P to the rear side, the forward component tensile force $T_V$ is larger than the outward component tensile force $T_H$. This allows the forward component tensile force $T_V$ to act as a force separating the wing-shaped flaps from the surface of the sanitary napkin 1, facilitating smooth unfolding of the wing-shaped flaps W.

As shown in FIG. 2, a second fixing region 21 is formed at the forward of the sanitary napkin 1 as a fixing region of the packaging sheet 16, the body releasing material 11, and the wing release material 12. In the second fixing region 21, the forward end of the body release material 11 is extended forward of the wing release material 12. The second fixing region 21 is formed across the body release material 11 and the wing release material 12 to fix the body release material 11, the wing release material 12, and the packaging sheet 16. The second fixing region 21 may be formed near the first fixing region 20 or continuously from the forward end of the first fixing region 20. The second fixing region 21 is formed across the body release material 11 and thus is smaller in width than the first fixing region 20.

Since the second fixing region 21 is provided, the body release material 11 can be peeled sequentially from the forward end, facilitating smooth peeling. Since the second fixing region 21 is formed across the body release material 11 and the wing release material 12, the joining state of the body release material 11, the wing release material 12, and the packaging sheet 16 can be reliably maintained in a manufacturing process of the napkin, thereby preventing wrinkles and bending on the release materials 11 and 12 and the packaging sheet 16.

The forward edge of the second fixing region 21 is preferably located forward of the forward edges of the body-fixing adhesive layers 9. Thus, the body release material 11 smoothly starts peeling off from the body-fixing adhesive layers 9.

In addition to the first fixing region 20 and the second fixing region 21, fixing regions for the packaging sheet 16, the body release material 11, and the wing release material 12 can be formed at any proper positions. In the example of FIG. 2, the rear side of the napkin 1 has fixing regions 22 for fixing the body release material 11 and the packaging sheet 16.

The invention claimed is:

1. An individually packaged absorbent article, the absorbent article comprising wing-shaped flaps formed on respective sides of a body having a front end and a back end and including an absorbing body between a permeable front-surface sheet and an impermeable back-surface sheet, the wing-shaped flaps being fixed so as to wrap laterally around a crotch of an undergarment upon attachment, the absorbent article further comprising: body-fixing adhesive layers formed on a surface of the impermeable back-surface sheet side of the body; and wing-fixing adhesive layers formed on surfaces of the impermeable back-surface sheet side of the wing-shaped flaps, wherein in a packaged state, the body-fixing adhesive layers are covered with a body release material, and the fixing adhesive layers formed on the wing-shaped flaps are covered with a wing release material extended in a width direction, the wing-shaped flaps are folded to the permeable front-surface sheet side with the wing release material, a packaging material is fixed at least to the wing release material, the ends of the wing-shaped flaps overlap on the permeable front-surface sheet side, the overlapping ends of the wing-shaped flaps are directly joined to each other with a wing-temporarily-fixing adhesive layer or indirectly joined through the wing release material so as to be peeled off, and the wing release material and the packaging material are fixed by a first fixing region that includes portions around folding lines of the wing-shaped flaps and is formed over forward end positions of the folding lines of the wing-shaped flaps in a longitudinal direction.

2. The individually packaged absorbent article according to claim 1, wherein the first fixing region includes the vicinity inside the folding lines of the wing-shaped flaps, within 10 mm from the folding lines.

3. The individually packaged absorbent article according to claim 1, wherein the first fixing region is continuously formed in a section including the portions around the folding lines in the width direction of the absorbent article, or the first fixing region is formed to be separated into at least two regions including at least both sides of the section.

4. The individually packaged absorbent article according to claim 1, wherein the wing-fixing adhesive layer is located at a rear portion of the wing-shaped flap, and the wing-fixing adhesive layer is formed with a clearance of at least 30 mm from the forward end position of the folding line to the rear edge of the wing-shaped flap.

5. The individually packaged absorbent article according to claim 1, further comprising a second fixing region in which a forward end of the body release material extends forward of the wing release material, the second fixing region being formed across the body release material and the wing release material to fix the body release material, the wing release material, and the packaging material.

6. The individually packaged absorbent article according to claim 1, further comprising a wing-temporarily-fixing adhesive layer joining the wing-shaped flaps and having an adhesive strength lower than an adhesive strength of the wing-fixing adhesive layer and the wing release material.

* * * * *